United States Patent [19]

Biermacher

[11] 4,116,837
[45] Sep. 26, 1978

[54] HIGH PRESSURE LIQUID CHROMATOGRAPHY APPARATUS

[75] Inventor: John J. Biermacher, Kalamazoo, Mich.

[73] Assignee: The Upjohn Company, Kalamazoo, Mich.

[21] Appl. No.: 869,020

[22] Filed: Jan. 12, 1978

[51] Int. Cl.² .............................................. B01D 15/08
[52] U.S. Cl. ................................. 210/198 C; 210/446
[58] Field of Search ................... 210/198 C, 411, 446; 55/386

[56] References Cited

U.S. PATENT DOCUMENTS

| | | | |
|---|---|---|---|
| 3,121,685 | 2/1964 | Hazell | 210/446 |
| 3,440,864 | 4/1964 | Blume | 210/198 C |
| 4,026,803 | 5/1977 | Abrahams | 210/198 C |
| 4,055,498 | 10/1977 | Rabnoti | 210/446 X |

Primary Examiner—John Adee
Attorney, Agent, or Firm—Blanchard, Flynn, Thiel, Boutell & Tanis

[57] ABSTRACT

A high pressure liquid chromatography apparatus having a detachable inline filter connected between the sample injection valve and the liquid chromatography column. The inline filter removes solid impurities from the liquid stream comprised of mobile phase and sample that is fed into the liquid chromatography column. If the inline filter becomes plugged, it can be detached from the sample injection valve and the liquid chromatography column and then cleaned by backwashing. The inline filter has a low dead volume and good filtration geometry so that the sharpness of the peaks of the chromatogram are not adversely affected to a significant degree by the use of the inline filter.

8 Claims, 3 Drawing Figures

HIGH PRESSURE LIQUID CHROMATOGRAPHY APPARATUS

BACKGROUND OF THE INVENTION

Field of the Invention

This invention relates to a high pressure liquid chromatography apparatus having an improved inline filter connected between the sample injection valve and the inlet to the liquid chromatography column.

In the high pressure liquid chromatography apparatuses, there is provided a sample injection valve for injecting the sample to be chromatographed into the mobile phase. The liquid stream is comprised of the mobile phase and the sample. The liquid stream flows from the sample injection valve into the liquid chromatography column. The column itself is usually provided with an internal sintered frit, as a filter element, at the inlet end thereof to filter out solid particles in the inflowing liquid stream. When the liquid chromatography column inlet filter becomes plugged, it can be cleaned by backwashing, but in many cases the column packing is thereby partially leached out or the packing of the particles in the chromatography column is adversely altered. This renders the column incapable of further use and it must be repacked before it can be reused. Repacking of a liquid chromatography column is relatively expensive and it is desired to minimize the number of times that it must be done. In particular, it has been desired to provide an inline filter between the sample injection valve and the inlet to the liquid chromatography column, which filter can be removed for servicing without disturbing the liquid chromatography column including the packing therein.

It has been proposed to provide a separate inline filter between the sample injection valve and the inlet to a high pressure liquid chromatography column. FIG. 1 illustrates a prior art inline filter for high pressure liquid chromatography columns. This filter comprises a body 1 within which is received an inner piece 2, a filter element 3, an outer piece 4 and a cap 5. The filter element 3 is comprised of a stainless steel frit 6 housed in a polytetrafluoroethylene sleeve 7, which in turn has a gasket 8 surrounding its exterior. The sleeve 7 is received in the opposed recesses in the confronting ends of the pieces 2 and 4. The gasket 8 seals the radial zone between the opposing surfaces of the pieces 2 and 4. This construction is relatively expensive. It possesses a limited filtering area because the filter element 3 is of relatively small diameter. Also, the filter element 3 is usually replaced when it becomes plugged, rather than being cleaned by backwashing. The replacement of the filter element is a significant item of expense in the use of this device.

It is an object of this invention to provide an improved high pressure liquid chromatography apparatus having an improved inline filter, which filter is of simplified construction, which can easily be backwashed without exposing the column bed and which possesses a very low dead volume and good filtration geometry so as to minimize adverse effects on the sharpness of the chromatographic peaks.

DESCRIPTION OF THE PREFERRED EMBODIMENT

Figure 1:
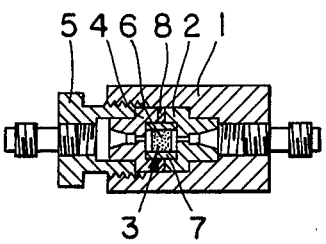
FIG. 1 is a cross-sectional view of a prior art inline filter for a high pressure liquid chromatography apparatus.
Figure 2:
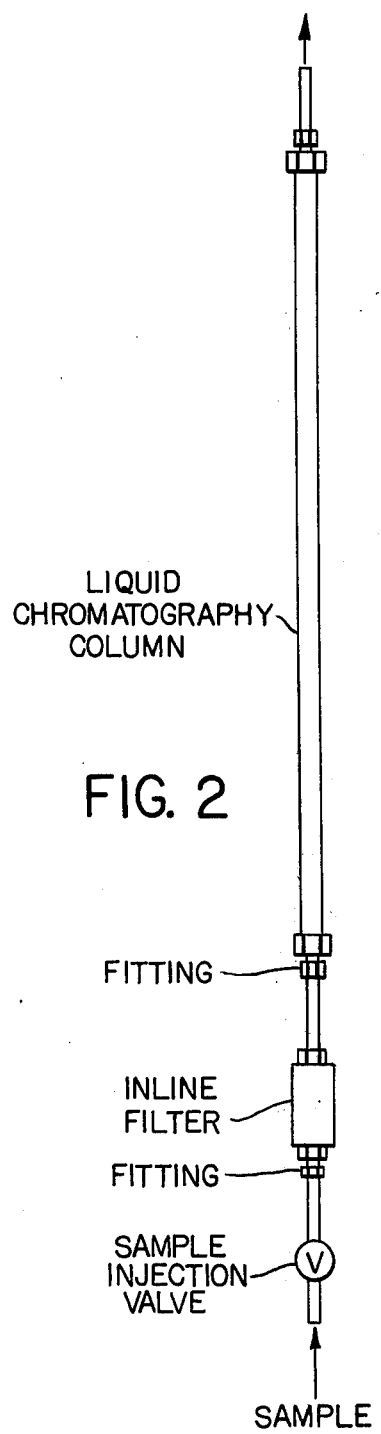
FIG. 2 is a schematic view of a high pressure liquid chromatography apparatus.

Referring to FIG. 2, there is shown a schematic view of a typical high pressure liquid chromatography apparatus. The liquid chromatography column is usually made of stainless steel and, typically, it has a length of about 25 to 100 centimeters and an internal diameter of from 2 to about 10 mm. The column is filled with packing particles of from about 5 to 50 micrometers in diameter. The inline filter has a filter element, such as polytetrafluoroethylene or stainless steel sintered frit, having a porosity of from about $\frac{1}{2}$ to about 10 micrometers, depending on the size of the column packing. It is customary to use a filter element made of stainless steel sintered frit having a porosity of about 2 micrometers for most practical applications. The sample liquid to be chromatographed is introduced into the system by means of the sample injection valve. Such sample injection valves and liquid chromatography columns are well-known commercially available items. The liquid sample is typically between about 1 and 20 microliters in volume and contains from about 0.1 to about 10 micrograms of the solute. It is very important to maintain the volume of the flow path for the sample, outside the liquid chromatography column itself, as small as possible in order to obtain a high resolution in the column. Thus, it is necessary to minimize the dead (unswept) volumes within the connectors and the inline filter and to provide good filtration geometry. It is an important feature of the present invention that the inline filter provides a very small dead volume and good filtration geometry.

As stated above, the liquid chromatography column, per se, and the sample injection valve, per se, are standard units available from a variety of different manufacturers. Normally, high pressure liquid chromatography columns and sample injection valves have standard fittings for receiving 1/16 inch OD stainless steel tubing having a very small bore size, such as a bore size of about 0.3 mm ID. It is an advantage of the invention that the inline filter can readily be used with the conventional commercially available liquid chromatography columns and sample injection valves. In particular, the inline filter can be directly connected between the outlet of the sample injection valve and the inlet of the liquid chromatography column, using conventional tube fittings.

It is customary in the art to use SWAGELOK (Trademark) tube fittings in order to connect tubes to sample injection valves and columns in high pressure liquid chromatography apparatuses. The conventional commercially available SWAGELOK tube fittings include a fitting for a 1/16-inch OD tube and a fitting for a $\frac{1}{4}$-inch OD tube. It is an advantage of the invention that the inline filter can be connected between the sample injection valve and the high pressure liquid chromatography column using the conventional commercially available SWAGELOK fittings, as described further hereinbelow. It will be understood, however, that the invention can be practiced using other types of tube fittings acceptable for use in high pressure liquid chromatography apparatuses.

Figure 3:
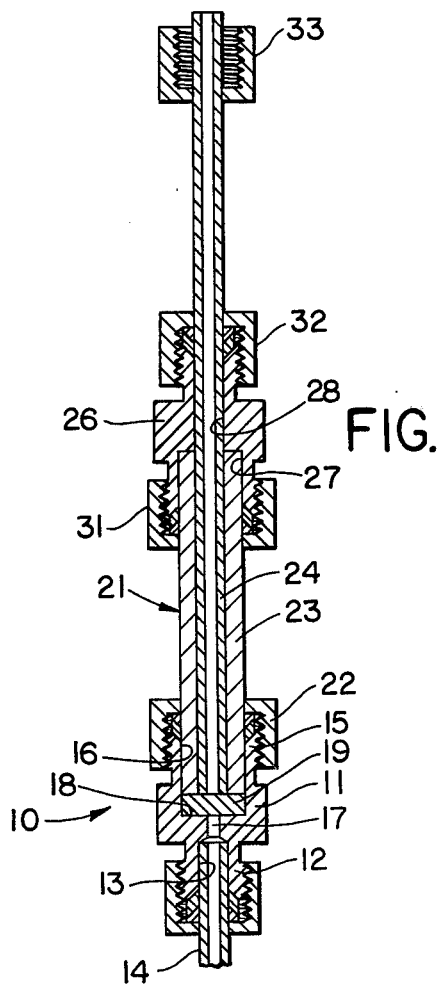
FIG. 3 is a cross-sectional view of an inline filter, according to the invention, for a high pressure liquid chromatography apparatus.

Referring to FIG. 3, the inline filter unit 10 comprises a body 11 having a first externally threaded nipple 12 which has a first internal recess 13 of relatively small diameter, usually a diameter of 1/16-inch, for receiving the end of a tube 14 which extends from the sample injection valve. As stated above, in a typical installation, the tube 14 has an outside diameter of 1/16-inch and an inside diameter of about 0.3 mm. The tube 14 is provided with a fitting member, threadedly engaged with the external threads on the nipple 12 whereby to provide a releasable sealed connection between the pipe 14 and the body 11 of the inline filter unit. For example, the inline filter unit 10 can be connected to the tube 14 by a SWAGELOK fitting. The body 11 also has a second externally threaded nipple 15 which has a second internal recess 16 of relatively larger diameter, usually a diameter of ¼-inch. The recesses 13 and 16 are of circular cross-section and they are coaxial with each other. A coaxial bore 17 extends between the inner ends of the recesses 13 and 16 to provide fluid flow communication therebetween. The bore 17 has substantially the same diameter as the internal diameter of the tube 14, for example, 0.3 mm.

A radially extending shoulder 18 is provided at the inner end of the recess 16. A filter element 19 in the form of a thin circular sheet, preferably made of stainless steel sintered frit, is firmly seated on the shoulder 18 and extends across the adjacent end of the bore 17 so that the liquid flowing from recess 13 into bore 17 and thence into the recess 16 is filtered by the filter element 19 so as to remove solid particles therefrom. In the typical embodiment of the invention referred to above, the filter element has a diameter of ¼-inch, a thickness of about 0.7 mm and a porosity of about 2 micrometers. It can be of the same structure as the stainless steel sintered frit conventionally used in the inlet of conventional commercially available liquid chromatography columns.

A second conduit 21 extends into the second recess 16 and its inner end bears against the surface of the filter element 19 in order to hold said filter element tightly against the shoulder 18. A nut 22 of a tube fitting, such as a SWAGELOK fitting, is sleeved on the second conduit 21 and is threaded onto the external threads of the second nipple 15 to provide a releaseable sealed connection between the second conduit 21 and the body 11.

The second conduit 21 comprises an outer circular tube 23 and an inner circular tube 24 tightly fitted inside said outer tube. The outer tube 23 has a relatively large outside diameter, such as ¼-inch in the typical embodiment of the invention described above, and said outer tube has an inner diameter of clearance space larger than the outside diameter of inner tube 24 so that the inner tube can be slid into the outer tube during assembly. The inner tube 24 has the same outside diameter and inside diameter as the tube 14, in the typical embodiment of the invention being described. The tubes 23 and 24 are soldered together at least at the corresponding ends thereof that abut against the surface of the filter element 19 to secure the tubes together and to prevent leakage therebetween. Said corresponding ends are ground to a smooth, planar finish so as to fit tightly against the planar surface of the filter element 19.

The inside diameter of the inner tube 23, the diameter of the bore 17 and the inside diameter of the tube 14 are essentially identical whereby to provide a flow path for the sample and mobile phase which is of uniform size throughout. Further, the tube 23, the bore 17 and the tube 14 are coaxial with one another so as to provide a straight line flow path for the liquid. In this way the inline filter has a very low dead volume and good geometry for filtration purposes.

The inline filter unit comprises a second body 26 having a first internal recess 27 of relatively large diameter for receiving the end of the outer tube 23. The body 26 has a through bore 28. The inner tube 24 extends through the bore 28. Fittings 31 and 32, such as SWAGELOK fittings, are provided to releasably sealingly connect the second body 26 to the outer tube 23 and also to sealingly secure the inner tube 24 to said second body. The remote end of the inner tube 24 has an end cap 33 of a fitting mounted thereon whereby the inline filter can be releasably attached to the inlet of the liquid chromatography column.

In use, the inline filter is connected at one end thereof to the conduit 14 leading from the sample injection valve and the other end thereof is connected to the inlet fitting of the high pressure liquid chromatography column. The liquid containing the sample to be chromatographed passes through the inline filter 10 so that any solid particles present therein are filtered by the filter element 19. The liquid then passes through the inner tube 24 and thence into the inlet of the liquid chromatography column. If the filter element 19 of the inline filter unit becomes plugged, the entire inline filter unit can be disconnected from the conduit 14 and from the inlet fitting of the liquid chromatography column. If desired or necessary, another like inline filter, which has already been cleaned, can be attached in place of the now removed inline filter unit so that the liquid chromatography apparatus can be continued to be used. The plugged filter unit is backwashed by connecting it to a suitable source of cleaning and backwashing liquid so that the cleaning liquid is flowed through the inline filter unit in a direction opposite to the normal direction of liquid flow through the inline filter when it is connected between the sample injection valve and the liquid chromatography column.

It is to be noted that there are no large void volumes or dead spaces in the inline filter unit according to the invention so that use of the inline filter does not significantly adversely affect the resolution achieved by the liquid chromatography column. The inline filter filters any solids that may flow through the line 14, due to impurities in the feed or possibly wear particles from the sample injection valve. When the filter becomes plugged, it can be easily cleaned by backwashing. This backwashing operation is completely independent of and does not affect the bed of packing particles in the liquid chromatography column. Another important feature of the invention is that standard commercially available tube fittings, tubes and filter elements are used so that it can be readily manufactured and it can easily be used with conventional sample injection valves and liquid chromatography columns.

The inline filter unit according to the invention also is advantageous because it prolongs the useful operating life before it is necessary to backwash or, when backwashing is not sufficiently effective, to replace the filter element 19. The initial flow of the liquid from bore 17 passes in straight-line flow axially through the central region of the filter element 19. As the pressure drop across the central region of the filter element 19 becomes higher owing to accumulation of solids on the central region of the surface thereof facing the bore 17, the liquid tends to flow radially outwardly from the bore 17 along shoulder 18 and thence flows axially through radially outer areas of the filter element that are not plugged with solids. In this regard, it is noted that the filter element 19 is a sintered stainless steel frit. Although it has a nominally planar surface abutting against shoulder 18, in actual fact there are microscopic cracks and crevices therein which permit some radial flow of the liquid along the shoulder 18. Thus, the radially outer areas of the filter element also are effective to filter the liquid whereby a longer useful life is obtained. Of course, at some time the pressure drop across the filter element reaches such a high level that it must then be backwashed or, when backwashing is ineffective, the filter element must be replaced.

Although a particular preferred embodiment of the invention has been described, the invention contemplates such changes or modifications therein as lie within the scope of the appended claims.

The embodiments of the invention in which an exclusive property or privilege is claimed are defined as follows:

1. A high pressure liquid chromatography apparatus comprising a sample injection valve; a first tube of relatively small external diameter leading from said sample injection valve; an inline filter comprising a body having a first recess of relatively small diameter, the adjacent end of said first tube being received in said first recess, and a first tube fitting releasably sealingly securing said adjacent end of said first tube in said first recess, said body having a second recess of relatively large diameter, a bore extending between the adjacent inner ends of said first and second recesses, a filter element seated on the inner end of said second recess and covering the adjacent end of said bore, a tubular conduit having one end thereof extending into said second recess and into abutting contact with said filter element, and a second tube fitting for releasably sealingly securing said one end of said tubular conduit in said second recess; and a liquid chromatography column having an inlet releasably sealingly connected to the other end of said tubular conduit, the internal diameters of said first tube and said tubular conduit and the diameter of said bore being substantially the same so as to define a flow passage of essentially the same diameter throughout its entire length with said flow passage being interrupted only by said filter element.

2. A high pressure liquid chromatography apparatus according to claim 1 wherein said first recess, said bore, said second recess, said first tube and said tubular conduit are coaxial with each other, and said filter element is a thin flat disc made of stainless steel sintered frit.

3. A high pressure liquid chromatography apparatus according to claim 2 wherein said tubular conduit comprises an outer tube and an inner tube tightly sealingly disposed within said outer tube, said inner tube having the same internal and external diameters as said first tube, a second body having a recess receiving the other end of said outer tube and a third tube fitting for releasably sealingly connecting said other end of said outer tube to said second body, said second body having a bore extending therethrough, said inner tube extending through said bore in said second body and beyond, said inner tube having a fourth tube fitting on the outer end thereof for sealingly connecting same to said inlet of said liquid chromatography column.

4. A high pressure liquid chromatography apparatus according to claim 3 wherein the diameter of said filter element is the same as the outside diameter of said outer tube.

5. An inline filter comprising a body having a first recess of relatively small diameter adapted for receiving the adjacent end of a first tube of relatively small external diameter, and a first tube fitting for releasably sealingly securing said adjacent end of the first tube in said first recess, said body having a second recess of relatively large diameter, a bore extending between the adjacent inner ends of said first and second recesses, a filter element seated on the inner end of said second recess and covering the adjacent end of said bore, a tubular conduit having one end thereof extending into said second recess and into abutting contact with said filter element, and a second tube fitting for releasably sealingly securing said one end of said tubular conduit in said second recess, the internal diameter of said tubular conduit and the diameter of said bore being substantially the same so as to define a flow passage of essentially the same diameter throughout its entire length with said flow passage being interrupted only by said filter element.

6. An inline filter according to claim 5 wherein said first recess, said bore, said second recess and said tubular conduit are coaxial with each other, and said filter element is a thin flat disc made of stainless steel sintered frit.

7. An inline filter according to claim 6 wherein said tubular conduit comprises an outer tube and an inner tube tightly sealingly disposed within said outer tube, said inner tube having the same internal diameter as said bore and the same external diameter as said first recess, a second body having a recess receiving the other end of said outer tube and a third tube fitting for releasably sealingly connecting said other end of said outer tube to said second body, said second body having a bore extending therethrough, said inner tube extending through said bore in said second body and beyond, said inner tube having a fourth tube fitting on the outer end thereof for sealingly connecting same to the inlet of a liquid chromatography column.

8. An inlet filter according to claim 7 wherein the diameter of said filter element is the same as the outside diameter of said outer tube.

* * * * *